United States Patent
Jones et al.

(10) Patent No.: US 11,070,762 B2
(45) Date of Patent: Jul. 20, 2021

(54) IMAGING APPARATUS FOR USE IN A ROBOTIC SURGERY SYSTEM

(71) Applicant: Titan Medical Inc., Toronto (CA)

(72) Inventors: Evan Rittenhouse Jones, Levittown, NY (US); Spencer James Costello, Levittown, NY (US)

(73) Assignee: TITAN MEDICAL INC., Toronto (CA)

( * ) Notice: Subject to any disclaimer, the term of this patent is extended or adjusted under 35 U.S.C. 154(b) by 0 days.

(21) Appl. No.: 16/598,751

(22) Filed: Oct. 10, 2019

(65) Prior Publication Data
US 2021/0112217 A1    Apr. 15, 2021

(51) Int. Cl.
*H04N 13/00* (2018.01)
*H04N 5/38* (2006.01)
(Continued)

(52) U.S. Cl.
CPC .............. *H04N 5/38* (2013.01); *A61B 1/005* (2013.01); *A61B 1/00009* (2013.01);
(Continued)

(58) Field of Classification Search
CPC .... H04N 5/38; H04N 5/2252; H04N 5/22521; H04N 5/2256; H04N 13/239; H04N 2005/2255; A61B 34/30; A61B 1/00018; A61B 1/051; A61B 1/00045; A61B 1/00078; A61B 1/005; A61B 1/0669; A61B 1/07; A61B 1/00009; A61B 1/00193; A61B 2034/301; A61B 90/361
(Continued)

(56) References Cited

U.S. PATENT DOCUMENTS

| 5,235,965 A | 8/1993 | Hiroya |
| 5,299,559 A | 4/1994 | Bruce |

(Continued)

FOREIGN PATENT DOCUMENTS

EP    0497347    *    1/1992

OTHER PUBLICATIONS

U.S. Appl. No. 16/156,651, filed Oct. 10, 2018, Genova et al.
(Continued)

*Primary Examiner* — Robert Chevalier

(57) ABSTRACT

A stereoscopic imaging apparatus for use in a robotic surgery system is disclosed and includes an elongate sheath having a bore. First and second image sensors are adjacently mounted at the distal end to capture high definition images from different perspective viewpoints for generating three-dimensional image information. The image sensors produce an unprocessed digital data signal representing the captured images. A wired signal line transmits the unprocessed digital data signals along the sheath to a proximal end to processing circuitry. The processing circuitry is configured to perform processing operations on the unprocessed digital data signals to produce respective video signals suitable for transmission to a host system or for driving a 3D display. A secondary camera is also disclosed and includes an elongate strip of circuit substrate sized for insertion through a narrow conduit, the strip of circuit substrate connecting between an image sensor and a processing circuit substrate.

23 Claims, 5 Drawing Sheets

(51) Int. Cl.

| | |
|---|---|
| *H04N 5/225* | (2006.01) |
| *A61B 34/30* | (2016.01) |
| *A61B 1/00* | (2006.01) |
| *A61B 1/05* | (2006.01) |
| *A61B 1/005* | (2006.01) |
| *A61B 1/06* | (2006.01) |
| *A61B 1/07* | (2006.01) |
| *H04N 13/239* | (2018.01) |
| *A61B 90/00* | (2016.01) |

(52) U.S. Cl.
CPC ...... *A61B 1/00018* (2013.01); *A61B 1/00045* (2013.01); *A61B 1/00078* (2013.01); *A61B 1/051* (2013.01); *A61B 1/0669* (2013.01); *A61B 1/07* (2013.01); *A61B 34/30* (2016.02); *H04N 5/2252* (2013.01); *H04N 5/2256* (2013.01); *H04N 5/22521* (2018.08); *H04N 13/239* (2018.05); *A61B 1/00193* (2013.01); *A61B 90/361* (2016.02); *A61B 2034/301* (2016.02); *H04N 2005/2255* (2013.01)

(58) Field of Classification Search
USPC ... 348/45, 42, 46, 47, 49, 51, 61, 65, 77, 85
See application file for complete search history.

(56) References Cited

U.S. PATENT DOCUMENTS

| | | | |
|---|---|---|---|
| 6,527,704 B1 | 3/2003 | Chang et al. | |
| 9,271,637 B2 | 3/2016 | Farr | |
| 9,492,065 B2 | 11/2016 | Tesar et al. | |
| 9,801,551 B2 | 10/2017 | Herzlinger et al. | |
| 9,877,744 B2 | 1/2018 | Cooper et al. | |
| 10,011,018 B2 | 7/2018 | McGrogan et al. | |
| 10,194,136 B2 | 1/2019 | Schwarz et al. | |
| 10,398,287 B1 * | 9/2019 | Genova | A61B 1/00135 |
| 2001/0031912 A1 | 10/2001 | Adler | |
| 2003/0233024 A1 | 12/2003 | Ando | |
| 2006/0252993 A1 | 11/2006 | Freed | |
| 2007/0043338 A1 | 2/2007 | Moll et al. | |
| 2007/0135803 A1 | 6/2007 | Belson | |
| 2007/0238927 A1 | 10/2007 | Ueno | |
| 2008/0033450 A1 | 2/2008 | Bayer et al. | |
| 2010/0274087 A1 | 10/2010 | Diolaiti et al. | |
| 2011/0208000 A1 | 8/2011 | Honda | |
| 2013/0282041 A1 | 10/2013 | Gunday et al. | |
| 2014/0005486 A1 | 1/2014 | Charles | |
| 2014/0107417 A1 | 4/2014 | McKinley et al. | |
| 2014/0180001 A1 | 6/2014 | von Grunberg et al. | |
| 2015/0141755 A1 | 5/2015 | Tesar | |
| 2015/0265143 A1 | 9/2015 | Yoon | |
| 2016/0255324 A1 | 9/2016 | Kazakevich et al. | |
| 2018/0054605 A1 * | 2/2018 | Grubner | H04N 13/239 |
| 2018/0140197 A1 | 5/2018 | Wang et al. | |
| 2019/0246887 A1 | 8/2019 | Oh | |
| 2020/0352069 A1 * | 11/2020 | Koo | H01R 43/205 |

OTHER PUBLICATIONS

U.S. Appl. No. 16/299,834, filed Mar. 12, 2019, Genova et al.
U.S. Appl. No. 16/435,170, filed Jun. 7, 2019, Genova et al.
U.S. Appl. No. 16/449,095, filed Jun. 21, 2019, Genova et al.
Advanced Sterilization Products, "Sterrad 100NX," downloaded on Oct. 8, 2018 from https://www.emea.aspjj.com/sites/aspjj.com.emea/files/pdf/STERRADFF_FamilyOfProducts_0.pdf, in 12 pages.
Intuitive Surgical, "da Vinci SP," downloaded on Oct. 9, 2018 from https://www.intuitivesurgical.com/sp/, in 5 pages.
Olympus America, "Rigid Laparoscopes," downloaded on Oct. 8, 2018 from http://medical.olympusamerica.com/products/rigid-laparoscopes in 2 pages.
International Search Report dated Jan. 18, 2021 and Written Opinion completed Dec. 21, 2020 corresponding to counterpart Int'l Patent Application PCT/CA2020/051344.

* cited by examiner

IMAGING APPARATUS FOR USE IN A ROBOTIC SURGERY SYSTEM

BACKGROUND

1. Field

This disclosure relates generally to imaging and more particularly to a stereoscopic imaging apparatus for use in generating images within a body cavity of a patient.

2. Description of Related Art

Stereoscopic imaging generally involves capturing a pair of images from spaced apart perspective viewpoints and processing the images to generate a three-dimensional (3D) view or 3D information based on a disparity between the pair of images. Conventional endoscopes used in medical and surgical procedures use relay lenses to convey captured light from a distal end of a narrow elongate tube inserted into a patient's body cavity to form an image at a proximal end of the tube. Alternatively, a small format image sensor capable of generating high resolution video signals may be used to capture an image at the distal end of the tube and to relay an image signal back to a host system for display. When implementing high definition imaging at high frame rates, image signals that are transmitted back to the host system by the image sensor have a relatively high data rate and there is consequently significant heat generation at the image sensor. The heat generation at the end of the tube may cause an unacceptable and/or unpredictable temperature increase of the distal end of the endoscope and within the body cavity of a patient.

SUMMARY

In accordance with one disclosed aspect there is provided a stereoscopic imaging apparatus for use in a robotic surgery system. The apparatus includes an elongate sheath having a bore extending therethrough. The sheath terminates in a distal end sized for insertion into a body cavity of a patient. First and second image sensors are adjacently mounted at the distal end of the sheath and oriented to capture high definition images of an object field from different perspective viewpoints for generating three-dimensional image information. Each of the first and second image sensors is configured to produce an unprocessed digital data signal representing the captured images. The apparatus also includes a wired signal line connected to transmit each of the unprocessed digital data signals from the first and second image sensors along the sheath to a proximal end thereof. The apparatus further includes processing circuitry disposed at the proximal end of the sheath and connected to the wired signal line to receive the unprocessed digital data signals from each of the first and second image sensors. The processing circuitry is configured to perform processing operations on each of the unprocessed digital data signals to produce respective video signals suitable for transmission to a host system for driving a display capable of three-dimensional information.

Each of the unprocessed digital data signals may have a bit rate higher than about 1 gigabit per second.

Each of the first and second image sensors have at about least 2,000,000 pixels.

The unprocessed digital data signal may include 10 bit pixel intensity values read out from the pixels of the respective first and second image sensors.

The unprocessed digital data signal may include a signal in accordance with a MIPI Camera Serial Interface protocol and the length of the sheath may be greater than 30 millimeters.

The apparatus of the length of the sheath may be at least about 800 millimeters.

The wired signal line may include a plurality of individual conductors including conductors for implementing at least one MIPI data lane for each image sensor, conductors for transmitting a synchronization clock signal between the processing circuitry and the first and second image sensors, and at least two conductors for carrying image sensor control signals.

The first and second image sensors may be mounted on a sensor circuit substrate disposed within the bore of the sheath and the wired signal line may include a plurality of individual conductors connected via the a sensor circuit substrate to unprocessed digital data outputs of the respective first and second image sensors.

The plurality of individual conductors of the wired signal line may be connected at the proximal end to a strip of circuit substrate sized to pass through the bore of the sheath, the strip of circuit substrate including a multiple pin connector for connecting to a corresponding multiple pin connector on a circuit substrate associated with the processing circuitry.

The apparatus may include a graphene sheet within the bore of the sheath, the graphene sheet being in thermal communication with the sensor circuit substrate and wrapped around at least a portion of a length of the wired signal line for channeling heat away from the distal end of the sheath.

The apparatus may include a heating element disposed at the distal end of the sheath and operably configured to selectively heat the distal end of the sheath to maintain the distal end of the sheath at a temperature that prevents formation of condensation.

The apparatus may include signal conditioning circuitry for conditioning the unprocessed digital data signals for transmission, the signal conditioning circuitry including at least one of conditioning circuitry at the distal end of the sheath between each of the first and second images sensors and the wired signal line, conditioning circuitry located partway along the sheath in-line with the wired signal line, or conditioning circuitry configured to re-condition the received unprocessed digital data signals prior to performing processing operations on the signals.

The processing circuitry may include circuitry that converts each of the unprocessed digital data signals into a serial digital interface (SDI) video signal for transmission to a host system.

The processing circuitry may include circuitry that converts each of the unprocessed digital data signals into a FPD link video signal for transmission to a host system.

The sheath may include one of a rigid sheath or a flexible sheath.

The sheath may include a flexible articulating portion which when actuated by the host system facilitates movement of the distal end of the sheath within the body cavity of a patient to orient the image sensors for image capture.

The apparatus may include a plurality of optical fibers extending through the sheath and terminating at the distal end, the plurality of optical fibers being operable to channel light from a distally located light source for illuminating the object field.

The first and second image sensors may be mounted on a sensor circuit substrate sized to occupy a central portion of the bore of the sheath and the plurality of optical fibers may terminate at regions between the sensor substrate and the sheath at the distal end of the sheath.

The sheath may have a generally circular cross section.

The sheath may have an outside diameter of less than about 10 millimeters.

Each of the image sensors may include imaging optics disposed in front of the respective faces of each of the image sensors and configured to capture light from the object field to form an image on the respective image sensors.

In accordance with another disclosed aspect there is provided an imaging apparatus. The apparatus includes an image sensor oriented to capture high definition images of an object field and configured to produce an unprocessed digital data signal representing the captured images. The apparatus also includes an elongate strip of circuit substrate sized for insertion through a narrow conduit. The image sensor is mounted at a distal end of the circuit substrate and connected to a plurality of conductors extending along the elongate circuit substrate to a proximal end thereof. The proximal end has a multiple pin connector for connecting to a corresponding multiple pin connector on a processing circuit substrate. The processing circuit substrate includes processing circuitry configured to receive and process the unprocessed digital data signal from the image sensor to produce a video signal suitable for transmission to a host system for driving a display.

The elongate strip of circuit substrate may have a length of at least about 20 centimeters and a width of less than about 4 millimeters.

In accordance with another disclosed aspect an insertion device for a robotic surgery apparatus includes an insertion section including first and second camera channels and at least one instrument channel extending along at least a portion of the insertion section. The first camera channel is configured to facilitate insertion and removal from the insertion section of the sheath and the first and second image sensors of as disclosed above for use as a primary camera. The second camera channel is configured to enclose the image sensor and elongate strip of circuit substrate disclosed above for use as a secondary camera. The at least one instrument channel is configured to permit insertion and removal of at least one surgical instrument from the insertion section. The apparatus also includes a housing attached to the insertion section. The housing includes a passage configured to permit at least a portion of the primary camera to pass through the housing into the first camera channel and exit the first camera channel, the housing configured to be removably attached to the robotic surgery apparatus. The secondary camera is configured to provide image data of a surgical site to facilitate insertion into the surgical site of at least one of the at least one surgical instrument or the primary camera.

Other aspects and features will become apparent to those ordinarily skilled in the art upon review of the following description of specific disclosed embodiments in conjunction with the accompanying figures.

BRIEF DESCRIPTION OF THE DRAWINGS

In drawings which illustrate disclosed embodiments.

DETAILED DESCRIPTION

Figure 1:
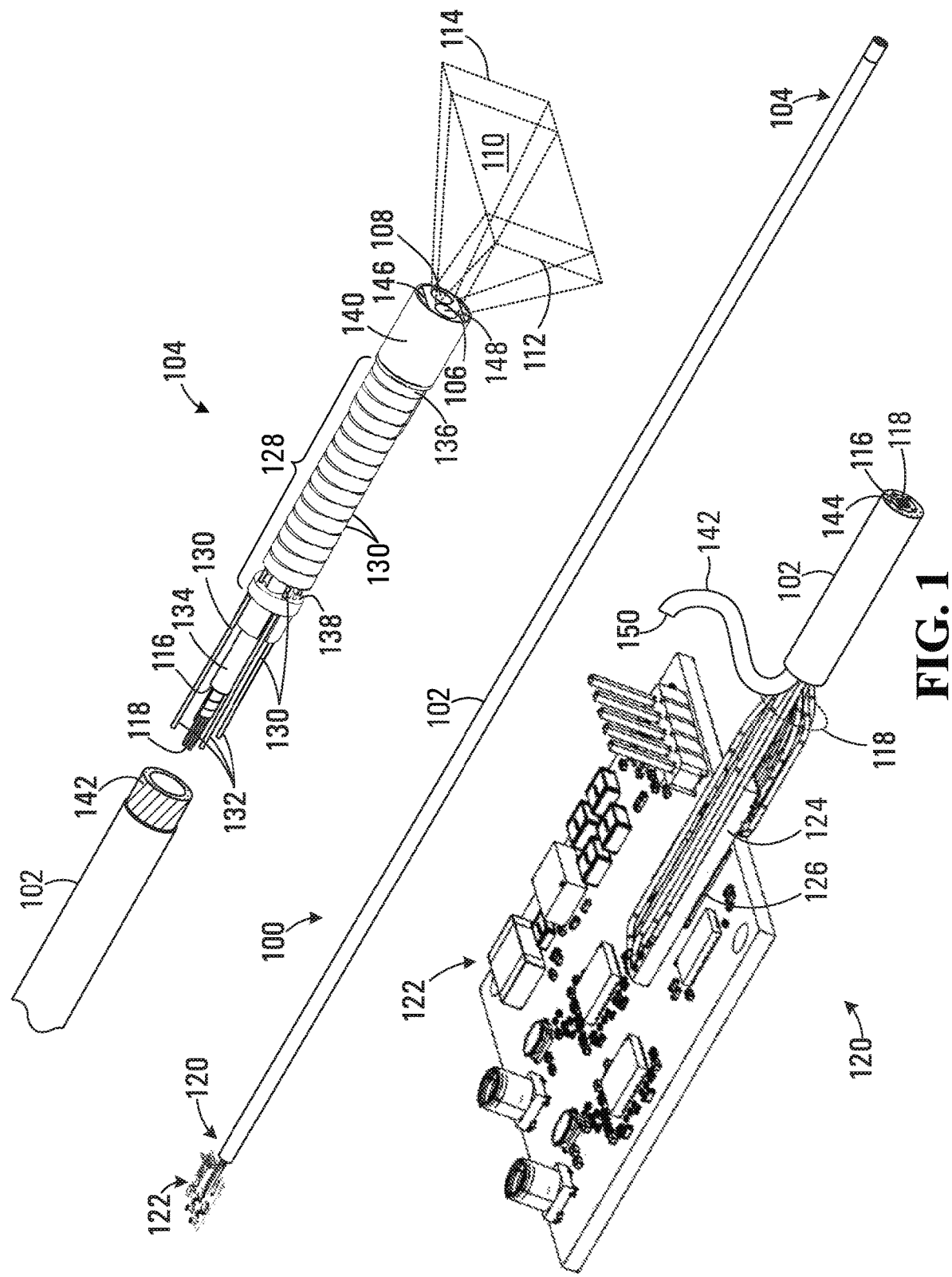
FIG. 1 is a perspective view of a stereoscopic imaging apparatus according to a first disclosed embodiment.

Referring to FIG. 1, a stereoscopic imaging apparatus according to a first disclosed embodiment is shown generally at 100. The apparatus 100 includes an elongate sheath 102. The sheath 102 terminates in a distal end 104 sized for insertion through an opening into a body cavity of a patient. The opening may be an incision made by a surgeon to permit access to the body cavity. In other embodiments the opening may be a natural orifice that permits access to the body cavity of the patient. The apparatus 100 may be part of a robotic surgery system for performing robotic surgery. In one embodiment the sheath 102 may be about 800 millimeters in length but in other embodiments may be longer or shorter.

The apparatus 100 further includes first and second image sensors at the distal end 104 of the elongate sheath 102. The distal end 104 is shown in greater detail in the insert in FIG. 1 with a portion of the sheath 102 removed. The first and second image sensors 106 and 108 are adjacently mounted at the distal end 104 of the sheath 102 within a sensor housing portion 140 at the end of the sheath. The first and second image sensors 106 and 108 are oriented to capture high definition images of an object field 110 from different perspective viewpoints 112 and 114 for generating three-dimensional (3D) image information.

The first and second image sensors 106 and 108 are each configured to produce an unprocessed digital data signal representing the images captured from the perspective viewpoints 112 and 114. Unprocessed digital video signals generally represent the actual intensity read out from each pixel on the image sensor. Some image sensors are configured to compress the video signal using a lossy compression method in which some of the video information may be removed. Otherwise known as a raw-video signal, an unprocessed digital data signal maintains the full integrity of the actual image information and preserves options for subsequent processing by the host system.

The apparatus 100 also includes a bore 116 extending through the elongate sheath 102 that accommodates a wired signal line 118 (shown in part in the insert of the distal end 104). The wired signal line 118 is connected to transmit each of the unprocessed digital data signals from the first and second image sensors 106 and 108 along the sheath 102 to a proximal end 120 of the sheath. The apparatus 100 also includes processing circuitry 122 disposed at the proximal end 120 of the sheath 102. The processing circuitry 122 is shown in greater detail in the insert in FIG. 1 and is connected to the wired signal line 118 via a strip of circuit substrate 124. Individual conductors of the wired signal line 118 are soldered to the strip of circuit substrate 124. The processing circuitry 122 includes a multiple pin connector 126 that connects to a corresponding multiple pin connector on the strip of circuit substrate 124. The strip of circuit substrate 124 is sized to pass through the bore 116 of the sheath 102 to facilitate threading of the wired signal line 118 through the sheath 102 from the distal end 104. The processing circuitry 122 thus receives the unprocessed digital data signals from each of the first and second image sensors 106 and 108 via the wired signal line 118 and is configured to perform processing operations on each of the unprocessed digital data signals to produce respective video signals suitable for transmission to a host system for driving a display (not shown) capable of displaying 3D information.

An advantage provided by the apparatus 100 is that the processing circuitry 122 is separated from the distal end 104 of the sheath 102 and the image sensors 106 and 108. The distal portion of the sheath 102 will generally be inserted into the patient's body cavity while the processing circuitry 122 remains outside the body cavity or otherwise away from the surgical site. Heat generated by the processing circuitry 122 while processing and transmitting the image signals is thus able to dissipate outside the body cavity of the patient (or otherwise away from the surgical site). Some heat is also generated by the first and second image sensors 106 and 108 but causes a lesser temperature increase than would be if the heat generated by the processing circuitry 122 were also to be dissipated proximate the distal end 104 of the sheath 102.

In the embodiment shown, the distal end 104 of the sheath 102 includes a flexible articulating portion 128, which includes a plurality of vertebra 130 that are moveable when actuated by a host system (not shown) by pushing and/or pulling on a plurality of control links 132. The flexible articulating portion 128 is shown in the distal end insert with one of the vertebra 130 omitted to reveal the underlying structure. In the embodiment shown, each vertebra 130 has a central opening for receiving a tube 134 that defines the bore 116 within the sheath 102. The plurality of control links 132 are routed through respective channels extending through the vertebrae and the distal ends of the control links are fixed at a last vertebra 136 in the flexible articulating portion 128. A face 138 of each vertebra includes a curved portion to accommodate movement with respect to adjacent vertebra so that the flexible articulating portion 128 is able to flex in all directions. The plurality of control links 132 are shown truncated in the insert of the distal end 104 but in practice extend through the length of the sheath 102 and are connected to an actuator drive of the host system at the proximal end 120. The vertebrae 130 move with respect to each other when actuated by the plurality of control links 132 cause movement of the distal end 104 of the sheath 102 such that the first and second image sensors 106 and 108 are oriented within the body cavity of the patient for image capture within the object field 110. In the embodiment shown, at least a portion of the tube 134 that passes through the flexible articulating portion 128 would be fabricated from a flexible material. However in some embodiments the entire tube 134 and the sheath 102 may be fabricated from flexible materials that allow the apparatus 100 to be flexed along its length.

In the embodiment shown, the apparatus 100 and sheath 102 have a generally circular cross section, and in one embodiment may have an outside diameter of less than about 10 millimeters. In the embodiment shown, the apparatus 100 also includes a fiber bundle 142 including a plurality of optical fibers. The fibers insert in an outer perimeter space 144 between the bore 116 and the sheath 102 at the proximal end 120 and are routed through the sheath to the distal end 104 where the fibers terminate in regions 146 and 148 above and below the image sensors 106 and 108. The fiber bundle 142 has an end 150 that couples to a distally located light source (not shown) that generates and couples light into the fiber bundle. The fiber bundle 142 guides the light along the sheath 102 to the regions 146 and 148 where the light is directed to illuminate the object field 110 for capturing images at the image sensors 106 and 108. In other embodiments, the fibers may terminate in other regions at the distal end 104, including, for example, at a plurality of regions.

Figure 2A:
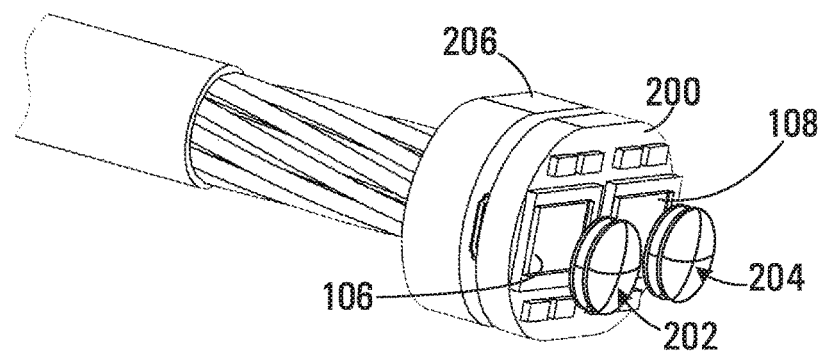
FIG. 2A is a perspective view of first and second image sensors of the stereoscopic imaging apparatus shown in FIG. 1.

Referring to FIG. 2A, the first and second image sensors 106 and 108 are shown with the sensor housing portion 140 and the remainder of the sheath 102 removed. The first and second image sensors 106 and 108 are substantially identical and are mounted on a common sensor circuit substrate 200. The sensor circuit substrate 200 is accommodated within a bore of the sensor housing portion 140 at the end of the sheath 102. Each of the image sensors 106 and 108 include a plurality of light sensitive elements or pixels. In one embodiment, the image sensors 106 and 108 may be implemented using a CMOS image sensor such as the OH02A10 available from OmniVision of Santa Clara, USA. The OH02A10 image sensor has 1.4 µm square pixels in a 1920×1080 array and the sensor has a ⅙ inch (i.e. 4.23 millimeters across its diagonal). Each image sensor 106 and 108 has associated imaging optics 202 and 204 disposed in front of the respective image sensors and configured to capture light from the object field 110 to form images on the respective image sensors. The OH02A10 image sensor is capable of a frame rate of 60 frames per second (fps) at full 1080p scan resolution thus providing high resolution video images.

Figure 2B:
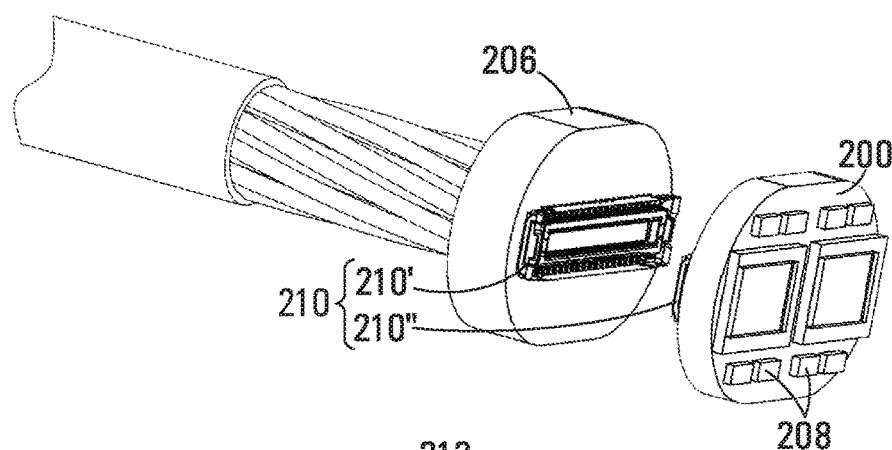
FIG. 2B is an exploded view of a sensor circuit substrate shown separated from a connector circuit substrate of the stereoscopic imaging apparatus shown in FIG. 1.

In this embodiment, the sensor circuit substrate 200 on which the first and second image sensors 106 and 108 are mounted is connected to a connector circuit substrate 206 via a multiple pin connector 210. Referring to FIG. 2B, the sensor circuit substrate 200 is shown separated from the connector circuit substrate 206. The connector 210 includes a connector portion 210' mounted on the connector circuit substrate and a corresponding connector portion 210" mounted on a rear surface of the sensor circuit substrate 200.

Figure 2C:
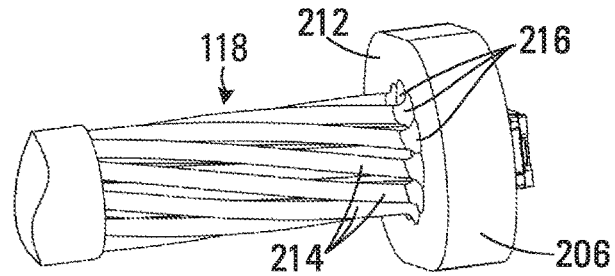
FIG. 2C is a rear view of the connector circuit substrate shown in FIG. 2B.

Referring to FIG. 2C, the wired signal line 118 is connected to a rear surface 212 of the connector circuit substrate 206. In this embodiment, the connection is formed by directly soldering individual conductors 214 in the wired signal line 118 at solder pads 216 on the rear surface 212 of the connector circuit substrate. Signals are routed to and from unprocessed digital data outputs of the respective first and second image sensors 106 and 108 via the sensor circuit substrate 200, the connector 210, and the connector circuit substrate 206, for transmission over the wired signal line 118 to the processing circuitry 122. The wired signal line 118 generally includes a plurality of conductors 214, including conductors for supplying power to the image sensors 106 and 108, conductors for transmitting image sensor control signals and a clock synchronization signal to the image sensors, and conductors that act as signal transmission lines for transmitting image signals to the processing circuitry 122 via the wired signal line. In the embodiment shown, the sensor circuit substrate 200 includes only passive electronic components 210 such as decoupling capacitors. In the embodiment shown, the only active components on the sensor circuit substrate 200 are the image sensors 106 and 108. In other embodiments, the sensor circuit substrate 200 or connector circuit substrate 206 may include additional signal conditioning circuitry for conditioning the signals to be transmitted to the processing circuitry 122 via the wired signal line 118.

Figure 2D:
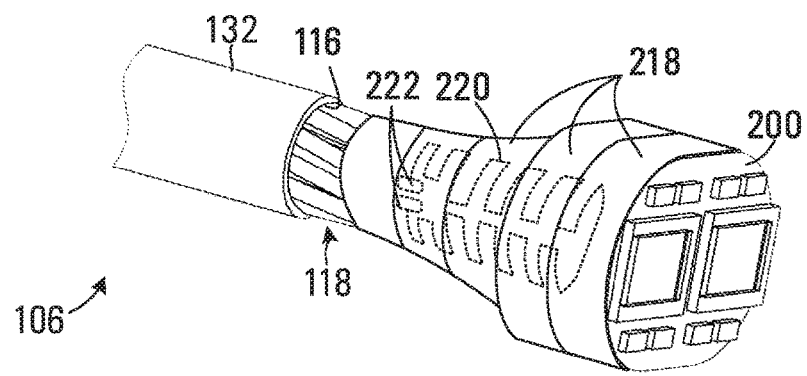
FIG. 2D is a further perspective view of first and second image sensors of the stereoscopic imaging apparatus shown in FIG. 1.

Referring to FIG. 2D, in this embodiment the sensor circuit substrate 200, connector circuit substrate 206, and wired signal line 118 are enclosed by a graphene sheet, a portion of which is shown at 218. The graphene sheet 218 extends into the bore 116 of the tube 134 and is wrapped about the sensor circuit substrate 200. The graphene sheet 218 channels heat away from the image sensors 106 and 108 along a length of the wired signal line 118. Graphene, having a high level of thermal conductivity, is effective at channeling the heat from the image sensors 106 and 108 along the sheath 102 away from a portion of the apparatus 100 that will be inserted into the patient's body cavity. Operation of image sensors and/or processing circuitry can cause a temperature increase, which if occurring at the distal end of the sheath 102 may affect sensitive tissues at the site of surgical operations.

In some embodiments the removal of heat by the graphene sheet 218 may reduce the temperature within the housing portion 140 of the sheath 102 to a point where condensation may form on the imaging optics 202 and 204 associated with the first and second image sensors 106 and 108. The body cavity temperature of the patient will typically be somewhere in the region of 37° C. and it would be desirable that the sensor housing portion 140 remain above this temperature to prevent condensation forming. Referring to FIG. 2D, in the embodiment shown, a heating element (or heater) 220 is provided at the distal end 104 of the sheath 102. The heating element 220 may be wrapped around the sensor circuit substrate 200 under the graphene sheet 218. Suitable heating elements including resistive traces formed on a flexible kapton sheet are available from Heatact Super Conductive Heat-Tech Co. Ltd of Taiwan or Embro GmbH, of Germany. The heating element 220 includes a pair of contact pads 222 that may be connected to receive a heating current via a pair of conductors that form part of the line 118. In one embodiment, a temperature at the first and second image sensors 106 and 108 may be monitored and the heating current supplied to the heating element 220 may be increased to heat the distal end 104 apparatus 100 when a risk of condensation is detected.

Figure 3:
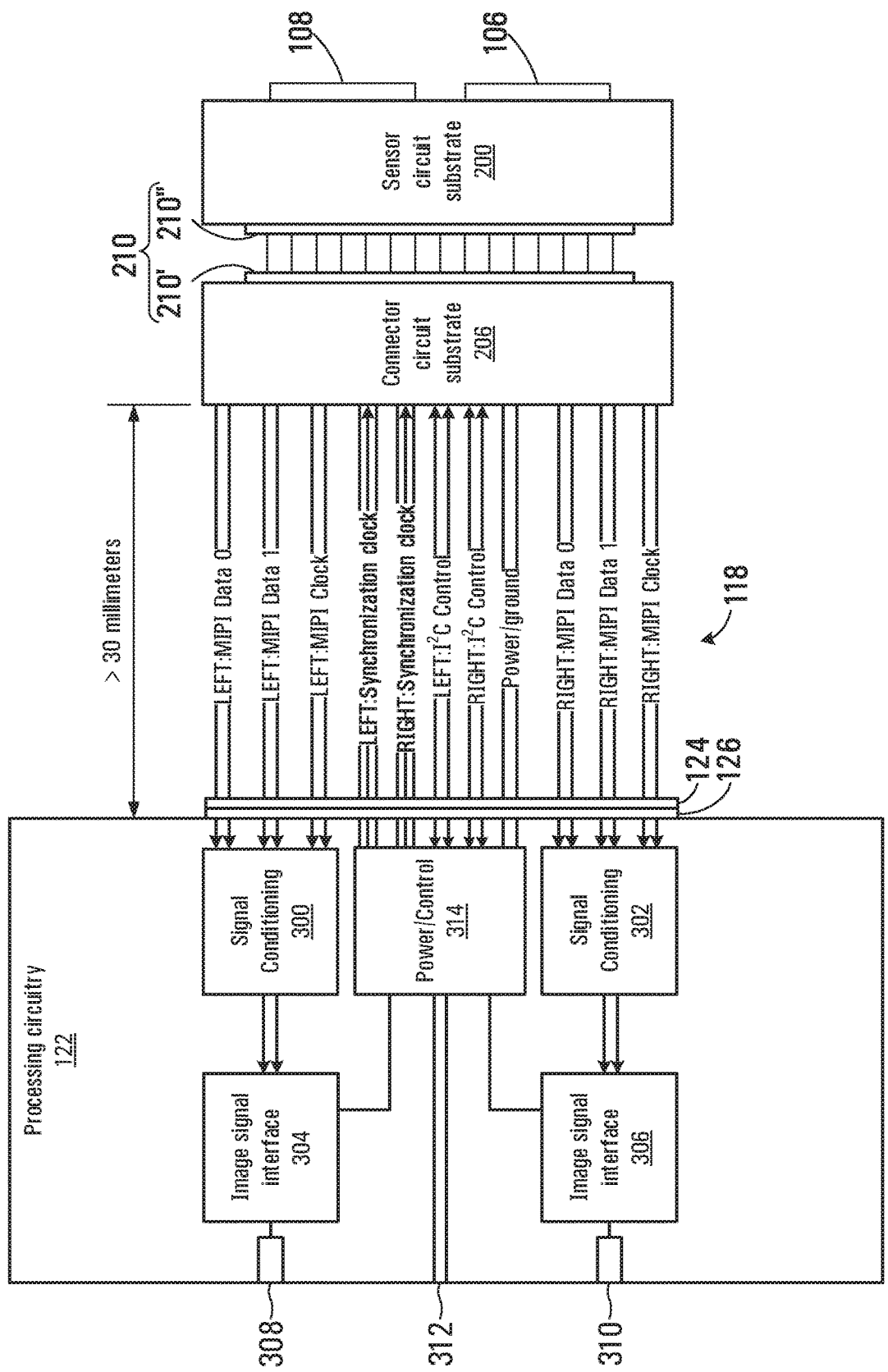
FIG. 3 is a schematic diagram of processing circuitry, the connector circuit substrate, and the sensor circuit substrate of the stereoscopic imaging apparatus shown in FIGS. 1, 2A and 2B.

A schematic diagram of the processing circuitry 122, connector circuit substrate 206, and sensor circuit substrate 200 is shown in FIG. 3. The first and second image sensors 106 and 108 are packaged for solder connection to the sensor circuit substrate 200 via a number of connection points that provide power and control signals to the sensor and read out image data. In the case of the Omnivision OH02A10 sensor, the package is a chip on polymer (CIP) package having 32 connections. The sensor circuit substrate 200 provides solder pads for soldering the sensors to the substrate such that the sensors can be mounted in alignment with each other and at a fixed lateral offset or stereoscopic separation distance. The sensor circuit substrate 200 further includes internal traces and via connections that route the necessary connections on the sensor to the connector portion 210". The connector circuit substrate 206 similarly includes traces and vias that route the connections from the connector portion 210', through the substrate, and out to the solder pads 216 on the rear surface 212 of the connector circuit substrate (shown in FIG. 2C).

As disclosed above, in this embodiment the sensor circuit substrate 200 and connector circuit substrate 206 only route connections between the image sensors 106, 108 and the wired signal line 118 and there is no active circuitry other than the image sensors mounted on these circuit substrates. In the embodiment shown, the sensor circuit substrate 200 and connector circuit substrate 206 are separate substrates, which facilitates separate fabrication and handling of the sensor circuit substrate 200 for protection of the sensitive CMOS image sensors 106, 108. In other embodiments, the sensor circuit substrate 200 and connector circuit substrate 206 may be fabricated as a single circuit substrate or the image sensors 106, 108 may be otherwise mounted and connected.

The wired signal line 118 includes the plurality of individual conductors 214 that extend between the solder pads 216 and the strip of circuit substrate 124, which connects to the multiple pin connector 126 on the processing circuitry 122. As disclosed above, image data from each of the first and second image sensors 106 and 108 are transmitted as unprocessed digital data signals to the processing circuitry 122 via the wired signal line 118. In the example of the Omnivision OH02A10 sensor, the unprocessed digital data signals comply with the MIPI CSI-2 transmission protocol, which is a camera serial interface protocol administered by the Mobile Industry Processor Interface (MIPI) Alliance. Other unprocessed data signal or raw image data protocols may be implemented depending on the selection of image sensors. Video signals may be transmitted using a variety of signal protocols such as Serial digital interface (SDI), Serial Peripheral Interface (SPI), $I^2C$ (Inter-Integrated Circuit), RGB video, or Low-voltage differential signaling (LVDS), some of which may be employed to transmit the video signals along the wired signal line 118.

In the embodiment shown in FIG. 3, the wired signal line 118 includes two twisted pairs of conductors for implementing two MIPI data lanes for each image sensor 106, 108. For the first (right hand side) image sensor 106, MIPI data lane 0 and MIPI data lane 1 are implemented, while for the second (left hand side) image sensor 108, MIPI data lane 0 and MIPI data lane 1 are implemented. The wired signal line 118 also includes a twisted pair of conductors for transmitting a clock associated with the MIPI signals for each of the sensors 106 and 108. In other embodiments, a single MIPI data lane or more than two MIPI data lanes may be implemented for each image sensor 106, 108. The MIPI CSI-2 protocol is generally used for short distance transmission between an imaging sensor and processing circuitry within in an imaging device, but in the apparatus 100 the distance over which transmission occurs is significantly increased. The wired signal line 118 also includes several power and ground conductors for delivering operating power to each of the sensors 106 and 108. The wired signal line 118 further includes a coaxial conductor for transmitting a synchronization clock signal between the processing circuitry 122 and each of the first and second image sensors 106 and 108. The wired signal line 118 also includes a two-wire inter-integrated circuit ($I^2C$) control line for carrying image sensor control signals between the processing circuitry 122 and each of the image sensors 106 and 108. The $I^2C$ control may be implemented using a serial data line (SDA) and a serial clock line (SCL) to control each of the image sensors 106 and 108. The image sensor control signals are used to set up and control parameters for image capture at the chip level.

An imaging apparatus used to generate views inside a patient's body cavity will generally have a length of at least 300 millimeters or greater between the distal end and the proximal end. In the example of the apparatus 100 shown in FIG. 1, the overall length is about 900 mm. The Omnivision OH02A10 sensor has 2,073,60 pixels (1920×1080) and an output format of 10 bit raw RGB data representing each pixel intensity. A single frame thus amounts to 20,736,000 bits of data, which at a frame rate of 60 frames per second represents a data rate of 1.24 gigabits per second for each image sensor. In the apparatus 100, there is a requirement to continuously transmit well in excess of 2 gigabits per second. This high data rate must be carried along the wired signal line 118 per sensor without significant signal degradation since image dropout in a medical device such as a surgical system is generally considered to be unacceptable. Data rates of well over 1 gigabit per second are not generally regarded to be successfully transmissible over MIPI CSI-2 data lanes when the length of transmission exceeds about 30 millimeters and thus the 900 mm transmission would be generally avoided.

The processing circuitry 122 is connected to the connector circuit substrate 206 via the wired signal line 118 at the multiple pin connector 126. In this embodiment, the processing circuitry 122 includes signal conditioning blocks 300 and 302 that receive and condition the unprocessed data signals (i.e. the MIPI data 0 and data 1 lane signals from the respective image sensors 106 and 108). In one embodiment, the MIPI data lane signals may be passed through a circuit that boosts the potentially weakened signals and to compensate for any degradation of the bits in each data stream. In this embodiment, the signal conditioning blocks 300 and 302 are implemented in the processing circuitry 122, which is disposed after the unprocessed data signals have been transmitted along the length of the wired signal line 118. In other embodiments, signal conditioning may additionally or alternatively be performed partway along the sheath 102 of the apparatus 100 in-line with the wired signal line 118. Alternatively, in other embodiments, signal conditioning may be performed at the sensor circuit substrate 200 or connector circuit substrate 206 should it be necessary to further extend transmission distance for the image signals. In other embodiments, signal conditioning functions may be omitted where the signal degradation during transmission over the wired signal line 118 is not of issue.

The conditioned signals are then passed by the signal conditioning blocks 300, 302 to respective image signal interface blocks 304 and 306 for conversion into video signals suitable for transmission over a longer distance to a host system. The image signal interface blocks 304 and 306 may each be implemented using a field-programmable gate array (FPGA) that performs a signal format conversion between the unprocessed signal format and a format suitable for transmission to a host system. The FPGA generally combines the MIPI data lane 0 and 1 streams and formats the signal into a video signal that can be transmitted over a greater distance to a host system and/or displayed on a 3D capable display. The processing circuitry 122 further includes ports 308 and 310 for connecting the apparatus 100 to enable a host system to receive the processed and formatted video image signals for display and/or further processing. The image signal interface blocks 304 and 306 may optionally perform other image processing functions on the signals such as filtering, white balance, color control and correction, etc.

In one embodiment, the image signal interface blocks 304 and 306 may be configured to produce serialized signals that comply with a flat panel display (FPD)-Link signal transmission protocol, which can be transmitted to a host system over a coaxial signal line via the ports 308 and 310. For example, an interface implementing the FPD-Link III update to the protocol is able to transmit the video data signals and also embed clock signals and a bidirectional communication channel on the same signal line.

In another embodiment, the image signal interface blocks 304 and 306 process and format the image data from each image sensor 106 and 108 into a 3G serial digital interface (SDI) serial data stream and the ports 308 and 310 are implemented as BNC connectors that connect to coaxial cables for carrying the first (right) and second (left) image sensor SDI serial data streams to the host system or display. SDI is a family of digital video interfaces commonly used for transmitting broadcast-grade video.

The processing circuitry 122 also receives a power feed at a connector 312 and further includes a power and control block 314, which is configured to receive the power feed and to supply power to the image sensors 106 and 108. The power and control block 314 also provides a control interface for sending imaging commands between a host system and the image sensors 106 and 108. In the embodiment shown, where the image signal interface blocks 304 and 306 implement the FPD-link III protocol, the bidirectional communication channel may be exploited to transmit image sensor control commands to the first and second image sensors 106 and 108 via the ports 308 and 310. In this case, the image signal interface blocks 304 and 306 are further configured to detect image sensor command signals on the bi-directional communication channel and to forward these command signals to the power and control block 314. The power and control block 314 acts as an interface for transmission of the commands to the respective image sensors 106 and 108 via the PC control signal conductors within the wired signal line 118.

Figure 4:
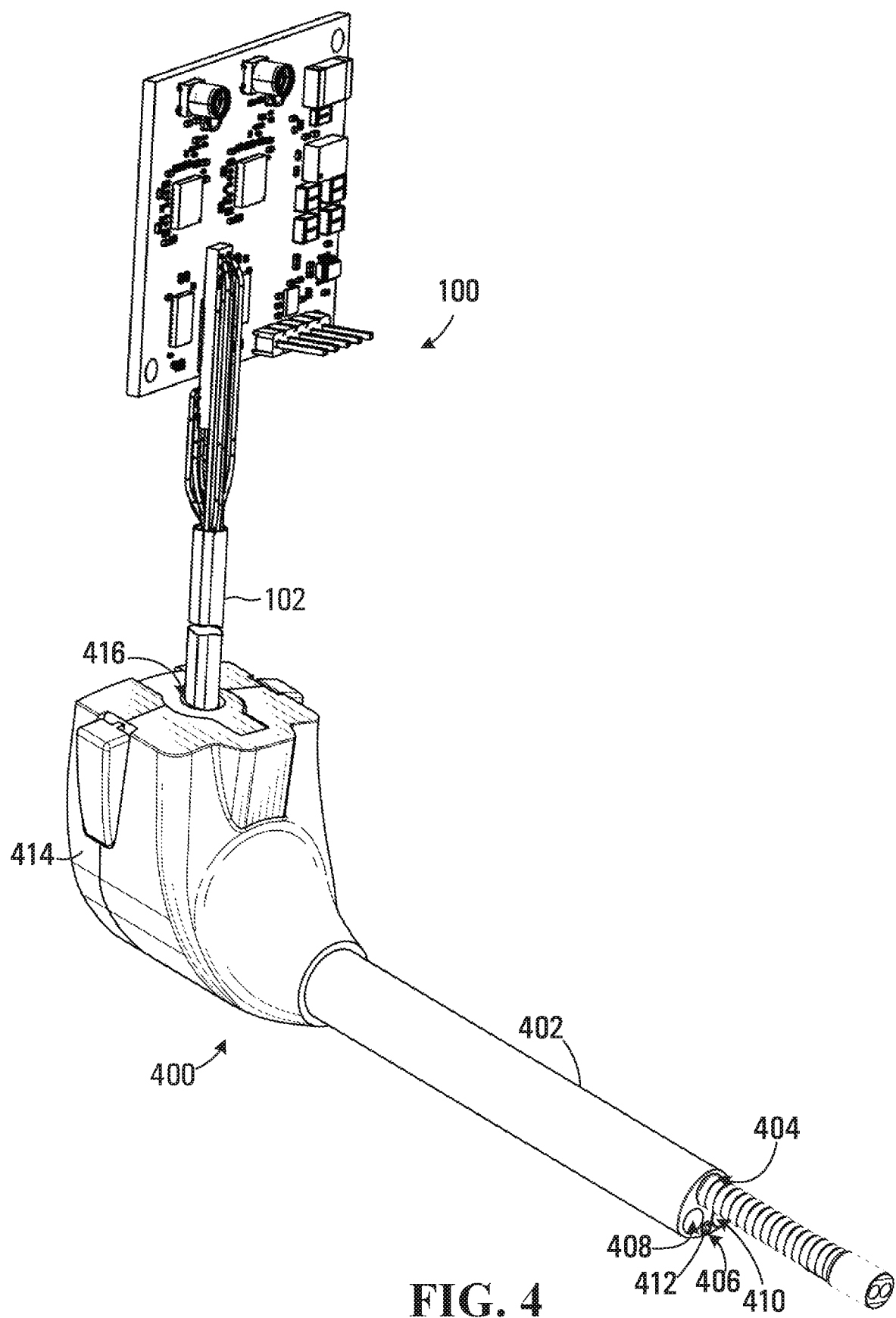
FIG. 4 is a perspective view of an insertion device through which the stereoscopic imaging apparatus shown in FIG. 1 is inserted.

Referring to FIG. 4, an insertion device for use with a robotic surgery apparatus (not shown) is shown at 400. The insertion device 400 includes an insertion section 402, which in turn includes first and second camera channels 404 and 406 for receiving a camera, such as the imaging apparatus 100. The insertion section 402 also includes one or more instrument channels (in this case instrument channels 408 and 410) that extend along at least a portion of the insertion section 402. The insertion section 402 is inserted into a body cavity of a patient and instruments (manual laparoscopic or robotic) are inserted through the instrument channels 408 and 410 to perform surgical operations within the body cavity. The insertion device 400 also includes a housing 414 attached to the insertion section 402. The housing 414 includes a passage 416 configured to permit at least a portion of the sheath 102 of the apparatus 100 to pass through the housing into the first camera channel 404 and to exit the first camera channel. The imaging apparatus 100 acts as a primary camera for producing 3D stereoscopic images of the body cavity. The second camera channel 406 receives a secondary camera 412, which provides 2D image data of a surgical site within the body cavity to facilitate insertion into the surgical site of surgical instruments through the instrument channels 408 and 410. The secondary camera 412 generates images of the body cavity of the patient prior to the apparatus 100 being inserted to provide the surgeon with a view of the surgical site for insertion of the instruments and the primary camera apparatus 100. The insertion device 400 is described in more detail in commonly owned patent application entitled "SYSTEMS, METHODS, AND APPARATUSES FOR CAPTURING IMAGES DURING A MEDICAL PROCEDURE", filed on Jun. 21, 2019 as U.S. patent application Ser. No. 16/449,095 and in commonly owned U.S. Pat. No. 10,398,287 entitled "CAMERA POSITIONING SYSTEM, METHOD, AND APPARATUS FOR CAPTURING IMAGES DURING A MEDICAL PROCEDURE", both of which are incorporated herein by reference in their entirety.

Figure 5:
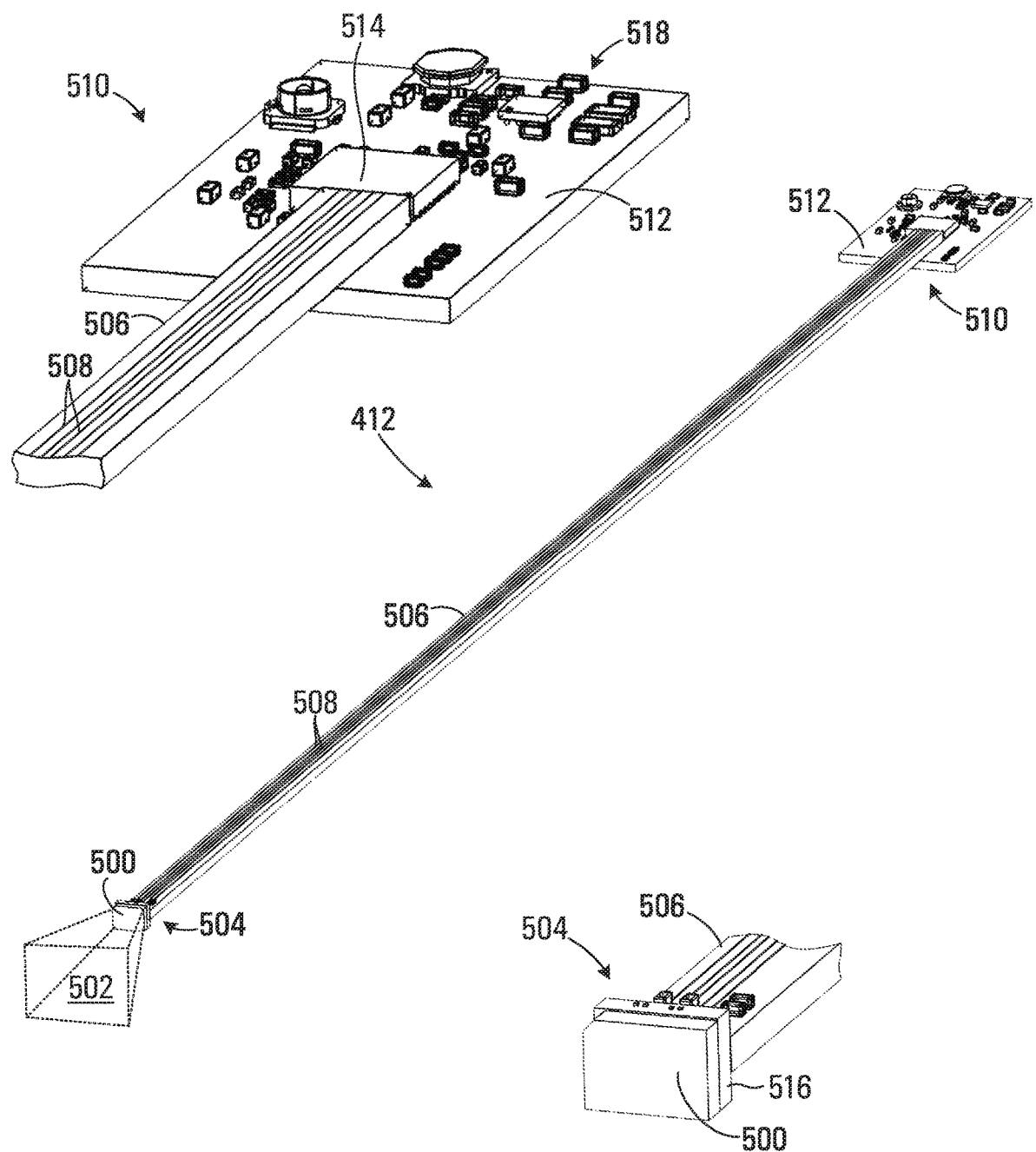
FIG. 5 is a perspective view of a secondary camera used in the insertion device shown in FIG. 4.

An embodiment of the secondary camera 412 is shown in FIG. 5. Referring to FIG. 5, in the embodiment shown, the secondary camera 412 includes an image sensor 500 oriented to capture high definition images of an object field 502. The image sensor 500 is mounted at a distal end 504 of an elongate strip of circuit substrate 506. The circuit substrate 506 includes a plurality of conductors 508 extending along the circuit substrate to a proximal end 510. The secondary camera 412 includes a processing circuit substrate 512, shown in greater detail in an insert in FIG. 5. The processing circuit substrate 512 includes a multiple pin connector 514, which is configured to receive and connect to the circuit substrate 506. The circuit substrate 506 includes a plurality of conductors 508 on the elongate circuit substrate 506 that form a connector at the proximal end of the strip. In some embodiments, two image sensors may be mounted at the distal end 504 to capture stereoscopic image data.

The distal end 504 of the secondary camera 412 is shown in greater detail in an insert in FIG. 5. In the embodiment shown, the image sensor 500 is connected to a sensor circuit substrate 516, which in turn is connected to the elongate circuit substrate 506. In one embodiment the connection between the sensor circuit substrate 516 and the elongate circuit substrate 506 may be a directly soldered connection. The image sensor 500 may produce an unprocessed digital data signal representing images captured from the object field 502 as described above in connection with the apparatus 100. The image sensor 500 is connected via the sensor circuit substrate 516 to the conductors 508 on the circuit substrate 506. The elongate strip of circuit substrate 506 is sized for insertion through a narrow conduit such as the second camera channel 406 of the insertion device 400 shown in FIG. 4. In some cases, the width (or diameter) of the conduit can be about 4 millimeters. In some embodiments, the secondary camera 412 may be removably insertable through the secondary camera channel 406. As an example, this would allow replacement of the secondary camera with another camera capable of capturing non-visible light (such as infrared light or the like). Alternatively the secondary camera may be replaced with a surgical instrument or other accessory.

The processing circuit substrate 512 includes processing circuitry 518 configured to receive and process the unprocessed digital data signal from the image sensor 500 to produce a video signal suitable for transmission to a host system for driving a display. In one embodiment, the elongate strip of circuit substrate 506 has a length of about 20 centimeters and a width of about 4 millimeters. In other embodiments, the circuit substrate 506 may have a length of greater than 20 centimeters and may be wider or narrower than 4 millimeters. The elongate circuit substrate 506 and image sensor 500 may be fabricated as a module that facilitates insertion of the proximal end 510 through the second camera channel 406 in the insertion section 402 of the insertion device 400. Once inserted, the camera module may be connected to the multiple pin connectors 514 at the proximal end.

The above embodiments of both the 3D stereoscopic primary imaging apparatus 100 and the secondary camera 412 provide for separation between the image sensors and the processing circuitry while facilitating relatively convenient handling during manufacture and subsequent use. The transmission of unprocessed raw image data from the sensor chips to the processing circuitry over a longer than conventional distance separates heat sources that would otherwise be in close proximity to the portions of the imaging apparatus 100 and secondary camera 412 that are inserted into the body cavity of the patient.

While specific embodiments have been described and illustrated, such embodiments should be considered illustrative only and not as limiting the disclosed embodiments as construed in accordance with the accompanying claims.

What is claimed is:

1. A stereoscopic imaging apparatus for use in a robotic surgery system, the apparatus comprising:
   an elongate sheath with a bore extending therethrough, the sheath terminating in a distal end sized for insertion into a body cavity of a patient;
   first and second image sensors adjacently mounted at the distal end of the sheath and oriented to capture high definition images of an object field from different perspective viewpoints for generating three-dimensional image information, each of the first and second image sensors configured to produce an unprocessed digital data signal representing the captured images;
   a wired signal line configured to transmit the unprocessed digital data signals from each of the first and second image sensors along the sheath to a proximal end thereof; and
   processing circuitry disposed at the proximal end of the sheath and connected to the wired signal line to receive the unprocessed digital data signals from each of the first and second image sensors, the processing circuitry configured to perform processing operations on each of the unprocessed digital data signals to produce respective video signals for transmission to a host system and driving a display configured to display three-dimensional information, wherein at least one unprocessed digital data signal includes a signal in accordance with a Mobile Industry Processor Interface (MIPI) Camera Serial Interface protocol, and wherein the length of the sheath is greater than 30 millimeters.

2. The apparatus of claim 1 wherein a bit rate of each of the unprocessed digital data signals is higher than about 1 gigabit per second.

3. The apparatus of claim 1 wherein each of the first and second image sensors include at least about 2,000,000 pixels.

4. The apparatus of claim 3 wherein the at least one unprocessed digital data signal comprises 10 bit pixel intensity values read out from the pixels of the respective first and second image sensors.

5. The apparatus of claim 1 wherein the length of the sheath is at least about 800 millimeters.

6. The apparatus of claim 1 wherein the wired signal line comprises a plurality of individual conductors including:
   conductors for implementing at least one Mobile Industry Processor Interface (MIPI) data lane for each image sensor;
   conductors for transmitting a synchronization clock signal between the processing circuitry and the first and second image sensors; and
   at least two conductors for carrying image sensor control signals.

7. A stereoscopic imaging apparatus for use in a robotic surgery system, the apparatus comprising:
   an elongate sheath with a bore extending therethrough, the sheath terminating in a distal end sized for insertion into a body cavity of a patient;
   first and second image sensors adjacently mounted at the distal end of the sheath and oriented to capture high definition images of an object field from different perspective viewpoints for generating three-dimensional image information, each of the first and second image sensors configured to produce an unprocessed digital data signal representing the captured images, wherein the first and second image sensors are mounted on a sensor circuit substrate disposed within the bore of the sheath;

a wired signal line configured to transmit the unprocessed digital data signals from each of the first and second image sensors along the sheath to a proximal end thereof, wherein the wired signal line comprises a plurality of individual conductors connected via the sensor circuit substrate to the unprocessed digital data outputs of the respective first and second image sensors; and processing circuitry disposed at the proximal end of the sheath and connected to the wired signal line to receive the unprocessed digital data signals from each of the first and second image sensors, the processing circuitry configured to perform processing operations on each of the unprocessed digital data signals to produce respective video signals for transmission to a host system and driving a display configured to display three-dimensional information.

8. The apparatus of claim 7 wherein the plurality of individual conductors of the wired signal line are connected at the proximal end to a strip of the sensor circuit substrate sized to pass through the bore of the sheath, the strip of the sensor circuit substrate including a multiple pin connector for connecting to a corresponding multiple pin connector on a circuit substrate associated with the processing circuitry.

9. The apparatus of claim 7 further comprising a graphene sheet within the bore of the sheath, the graphene sheet being in thermal communication with the sensor circuit substrate and wrapped around at least a portion of a length of the wired signal line to channel heat away from the distal end of the sheath.

10. The apparatus of claim 9 further comprising a heater disposed at the distal end of the sheath and configured to selectively heat the distal end of the sheath to maintain the distal end of the sheath at a temperature that prevents formation of condensation.

11. The apparatus of claim 1 further comprising A stereoscopic imaging apparatus for use in a robotic surgery system, the apparatus comprising:

an elongate sheath with a bore extending therethrough, the sheath terminating in a distal end sized for insertion into a body cavity of a patient;

first and second image sensors adjacently mounted at the distal end of the sheath and oriented to capture high definition images of an object field from different perspective viewpoints for generating three-dimensional image information, each of the first and second image sensors configured to produce an unprocessed digital data signal representing the captured images;

a wired signal line configured to transmit the unprocessed digital data signals from each of the first and second image sensors along the sheath to a proximal end thereof;

processing circuitry disposed at the proximal end of the sheath and connected to the wired signal line to receive the unprocessed digital data signals from each of the first and second image sensors, the processing circuitry configured to perform processing operations on each of the unprocessed digital data signals to produce respective video signals for transmission to a host system and driving a display configured to display three-dimensional information; and signal conditioning circuitry configured to condition the unprocessed digital data signals for transmission, the signal conditioning circuitry comprising at least one of:
conditioning circuitry positioned at the distal end of the sheath between each of the first and second images sensors and the wired signal line;
conditioning circuitry located partway along the sheath in-line with the wired signal line; or
conditioning circuitry configured to re-condition the received unprocessed digital data signals prior to performing processing operations on the signals.

12. The apparatus of claim 1 wherein the processing circuitry is configured to convert each of the unprocessed digital data signals into a serial digital interface (SDI) video signal for transmission to the host system.

13. The apparatus of claim 1 wherein the processing circuitry is configured to convert each of the unprocessed digital data signals into a flat patent display (FPD) link video signal for transmission to the host system.

14. The apparatus of claim 1 wherein the sheath comprises one of a rigid sheath or a flexible sheath.

15. The apparatus of claim 1 wherein the sheath comprises a flexible articulating portion which, when actuated by the host system, facilitates movement of the distal end of the sheath within the body cavity of a patient to orient the image sensors for image capture.

16. A stereoscopic imaging apparatus for use in a robotic surgery system, the apparatus comprising:

an elongate sheath with a bore extending therethrough, the sheath terminating in a distal end sized for insertion into a body cavity of a patient;

first and second image sensors adjacently mounted at the distal end of the sheath and oriented to capture high definition images of an object field from different perspective viewpoints for generating three-dimensional image information, each of the first and second image sensors configured to produce an unprocessed digital data signal representing the captured images;

a wired signal line configured to transmit the unprocessed digital data signals from each of the first and second image sensors along the sheath to a proximal end thereof;

processing circuitry disposed at the proximal end of the sheath and connected to the wired signal line to receive the unprocessed digital data signals from each of the first and second image sensors, the processing circuitry configured to perform processing operations on each of the unprocessed digital data signals to produce respective video signals for transmission to a host system and driving a display configured to display three-dimensional information; and a plurality of optical fibers extending through the sheath and terminating at the distal end, the plurality of optical fibers configured to channel light from a distally located light source for illuminating the object field.

17. The apparatus of claim 16 wherein the first and second image sensors are mounted on a sensor circuit substrate sized to occupy a central portion of the bore of the sheath and wherein the plurality of optical fibers terminate at one or more regions between the sensor substrate and the sheath at the distal end of the sheath.

18. The apparatus of claim 1 wherein the sheath has a generally circular cross section.

19. The apparatus of claim 18 wherein an outside diameter of the sheath is less than about 10 millimeters.

20. A stereoscopic imaging apparatus for use in a robotic surgery system, the apparatus comprising:
an elongate sheath with a bore extending therethrough, the sheath terminating in a distal end sized for insertion into a body cavity of a patient;
first and second image sensors adjacently mounted at the distal end of the sheath and oriented to capture high definition images of an object field from different perspective viewpoints for generating three-dimensional image information, each of the first and second image sensors configured to produce an unprocessed digital data signal representing the captured images, wherein each of the image sensors include imaging optics disposed in front of the respective faces of each of the image sensors and configured to capture light from the object field to form an image on the respective image sensor;
a wired signal line configured to transmit the unprocessed digital data signals from each of the first and second image sensors along the sheath to a proximal end thereof; and
processing circuitry disposed at the proximal end of the sheath and connected to the wired signal line to receive the unprocessed digital data signals from each of the first and second image sensors, the processing circuitry configured to perform processing operations on each of the unprocessed digital data signals to produce respective video signals for transmission to a host system and driving a display configured to display three-dimensional information.

21. An imaging apparatus comprising:
an image sensor oriented to capture high definition images of an object field and configured to produce an unprocessed digital data signal representing the captured images; and
an elongate strip of circuit substrate sized for insertion through a conduit, the image sensor being mounted at a distal end of the circuit substrate and connected to a plurality of conductors extending along the elongate circuit substrate to a proximal end thereof, the proximal end including a multiple pin connector for connecting to a corresponding multiple pin connector on a processing circuit substrate, the processing circuit substrate including processing circuitry configured to receive and process the unprocessed digital data signal from the image sensor to produce a video signal for transmission to a host system and driving a display.

22. The apparatus of claim 21 wherein a length of the elongate strip of circuit substrate is at least about 20 centimeters and a width of the elongate strip of circuit substrate is less than about 4 millimeters.

23. An insertion device for a robotic surgery apparatus, the insertion device comprising:
an insertion section comprising first and second camera channels and at least one instrument channel extending along at least a portion of the insertion section, the first camera channel configured to facilitate insertion and removal from the insertion section of the sheath and the first and second image sensors of claim 1 for use as a primary camera, the second camera channel configured to enclose the image sensor and elongate strip of circuit substrate of claim 17 for use as a secondary camera, and the at least one instrument channel configured to permit insertion and removal of at least one surgical instrument from the insertion section; and
a housing attached to the insertion section, the housing comprising a passage configured to permit at least a portion of the primary camera to pass through the housing into the first camera channel and exit the first camera channel, the housing configured to be removably attached to the robotic surgery apparatus;
wherein the secondary camera is configured to provide image data of a surgical site to facilitate insertion into the surgical site of at least one of the at least one surgical instrument or the primary camera.

* * * * *